(12) United States Patent
Logan et al.

(10) Patent No.: US 12,144,752 B2
(45) Date of Patent: *Nov. 19, 2024

(54) STENT DELIVERY SYSTEMS

(71) Applicant: BOSTON SCIENTIFIC SCIMED, INC., Maple Grove, MN (US)

(72) Inventors: Brady Scott Logan, Maple Grove, MN (US); Jason T. Anderson, Deephaven, MN (US); Paul Michael Goudreau, Edina, MN (US); Andrew Nathaniel Smith, Brooklyn Center, MN (US); Ian Thomas Forte, Brooklyn Park, MN (US); Tyler Lorne Hebig, Wayzata, MN (US); Rowan Olund Hettel, Plymouth, MN (US); Ryan Dale Hendrickson, Albertville, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 100 days.

This patent is subject to a terminal disclaimer.

(21) Appl. No.: 18/107,304

(22) Filed: Feb. 8, 2023

(65) Prior Publication Data

US 2023/0181344 A1 Jun. 15, 2023

Related U.S. Application Data

(63) Continuation of application No. 16/790,560, filed on Feb. 13, 2020, now Pat. No. 11,602,447.

(Continued)

(51) Int. Cl.
*A61F 2/966* (2013.01)
*A61F 2/24* (2006.01)
(Continued)

(52) U.S. Cl.
CPC ............ *A61F 2/966* (2013.01); *A61F 2/2436* (2013.01); *A61F 2/95* (2013.01); *A61F 2/9517* (2020.05); *A61F 2/962* (2013.01)

(58) Field of Classification Search
CPC .......... A61F 2/95; A61F 2/9517; A61F 2/962; A61F 2/2436; A61F 2/966; A61M 25/0136; A61M 2025/1068; A61M 25/0113
See application file for complete search history.

(56) References Cited

U.S. PATENT DOCUMENTS

| 3,613,684 A | 10/1971 | Sheridan |
| 4,665,918 A | 5/1987 | Garza et al. |

(Continued)

FOREIGN PATENT DOCUMENTS

| EP | 0676936 A1 | 10/1995 |
| EP | 0684022 A2 | 11/1995 |

(Continued)

OTHER PUBLICATIONS

En.wikipedia.org. 2022. Polycarbonate—Wikipedia. [online] Available at: >https://en.wikipedia.org/wiki/Polycarbonate> pp. 1-7. (Year: printed 2022).

(Continued)

*Primary Examiner* — Mohamed G Gabr
*Assistant Examiner* — Andrew P. Restaino
(74) *Attorney, Agent, or Firm* — Seager, Tufte & Wickhem, LLP

(57) ABSTRACT

Stent delivery systems and methods for making and using stent delivery systems are disclosed. An example stent delivery system may include an inner member having a stent receiving region. A stent may be disposed along the stent receiving region. The system may also include a deployment sheath axially slidable relative to the inner member. The (Continued)

deployment sheath may have a proximal end region. A rack may be coupled to the proximal end region of the deployment sheath. An outer shaft may be disposed along at least a portion of the deployment sheath. The deployment sheath may be rotatable relative to the inner member, the outer shaft or both.

19 Claims, 14 Drawing Sheets

Related U.S. Application Data

(60) Provisional application No. 62/805,133, filed on Feb. 13, 2019.

(51) Int. Cl.
*A61F 2/95* (2013.01)
*A61F 2/962* (2013.01)

(56) References Cited

U.S. PATENT DOCUMENTS

| | | | |
|---|---|---|---|
| 4,732,152 A | 3/1988 | Wallsten et al. |
| 4,813,107 A | 3/1989 | Cetrone |
| 4,906,232 A | 3/1990 | Reynolds |
| 5,026,377 A | 6/1991 | Burton |
| 5,071,407 A | 12/1991 | Termin et al. |
| 5,158,548 A | 10/1992 | Lau et al. |
| 5,163,905 A | 11/1992 | Don Michael |
| 5,201,757 A | 4/1993 | Heyn et al. |
| 5,221,261 A | 6/1993 | Termin et al. |
| 5,238,004 A | 8/1993 | Sahatjian et al. |
| 5,346,471 A | 9/1994 | Raulerson |
| 5,378,239 A | 1/1995 | Termin et al. |
| 5,433,723 A | 7/1995 | Lindenberg et al. |
| 5,443,907 A | 8/1995 | Slaikeu et al. |
| 5,445,646 A | 8/1995 | Euteneuer et al. |
| 5,496,277 A | 3/1996 | Termin et al. |
| 5,534,007 A | 7/1996 | St. Germain et al. |
| 5,571,135 A | 11/1996 | Fraser et al. |
| 5,662,703 A | 9/1997 | Yurek et al. |
| 5,674,242 A | 10/1997 | Phan et al. |
| 5,690,644 A | 11/1997 | Yurek et al. |
| 5,695,499 A | 12/1997 | Helgerson et al. |
| 5,702,364 A | 12/1997 | Euteneuer et al. |
| 5,707,376 A | 1/1998 | Kavteladze et al. |
| 5,713,860 A | 2/1998 | Kaplan et al. |
| 5,733,267 A | 3/1998 | Del Toro |
| 5,755,777 A | 5/1998 | Chuter |
| 5,772,609 A | 6/1998 | Nguyen et al. |
| 5,772,669 A | 6/1998 | Vrba |
| 5,788,707 A | 8/1998 | Del Toro et al. |
| 5,830,181 A | 11/1998 | Thornton |
| 5,833,694 A | 11/1998 | Poncet |
| 5,833,706 A | 11/1998 | St. Germain et al. |
| 5,843,090 A | 12/1998 | Schuetz |
| 5,843,091 A | 12/1998 | Holsinger et al. |
| 5,882,347 A | 3/1999 | Mouris-Laan et al. |
| 5,891,154 A | 4/1999 | Loeffler |
| 5,906,619 A | 5/1999 | Olson et al. |
| 5,954,764 A | 9/1999 | Parodi |
| 5,957,930 A | 9/1999 | Vrba |
| 5,968,052 A * | 10/1999 | Sullivan, III | A61F 2/95 623/1.11 |
| 5,980,483 A | 11/1999 | Dimitri |
| 6,017,577 A | 1/2000 | Hostettler et al. |
| 6,019,778 A | 2/2000 | Wilson et al. |
| 6,033,413 A | 3/2000 | Mikus et al. |
| 6,059,813 A | 5/2000 | Vrba et al. |
| 6,117,140 A | 9/2000 | Munsinger |
| 6,120,522 A | 9/2000 | Vrba et al. |
| 6,123,723 A | 9/2000 | Konya et al. |
| 6,139,510 A | 10/2000 | Palermo |
| 6,139,524 A | 10/2000 | Killion |
| 6,176,849 B1 | 1/2001 | Yang et al. |
| 6,206,888 B1 | 3/2001 | Bicek et al. |
| 6,221,467 B1 | 4/2001 | Nazarova et al. |
| 6,238,410 B1 | 5/2001 | Vrba et al. |
| 6,254,609 B1 | 7/2001 | Vrba et al. |
| 6,287,329 B1 | 9/2001 | Duerig et al. |
| 6,322,586 B1 | 11/2001 | Monroe et al. |
| 6,330,884 B1 | 12/2001 | Kim |
| 6,331,184 B1 | 12/2001 | Abrams |
| 6,342,066 B1 | 1/2002 | Toro et al. |
| 6,355,060 B1 | 3/2002 | Lenker et al. |
| 6,375,676 B1 | 4/2002 | Cox |
| 6,379,365 B1 | 4/2002 | Diaz |
| 6,380,457 B1 | 4/2002 | Yurek et al. |
| 6,391,050 B1 | 5/2002 | Broome |
| 6,398,802 B1 | 6/2002 | Yee |
| 6,425,898 B1 | 7/2002 | Wilson et al. |
| 6,508,803 B1 | 1/2003 | Horikawa et al. |
| 6,514,228 B1 | 2/2003 | Hamilton et al. |
| 6,514,261 B1 | 2/2003 | Randall et al. |
| 6,544,278 B1 | 4/2003 | Vrba et al. |
| 6,576,006 B2 | 6/2003 | Limon et al. |
| 6,589,251 B2 | 7/2003 | Yee et al. |
| 6,602,226 B1 | 8/2003 | Smith et al. |
| 6,613,014 B1 | 9/2003 | Chi |
| 6,626,934 B2 | 9/2003 | Blaeser et al. |
| 6,669,716 B1 | 12/2003 | Gilson et al. |
| 6,726,712 B1 | 4/2004 | Raeder-Devens et al. |
| 6,726,714 B2 | 4/2004 | DiCaprio et al. |
| 6,736,839 B2 | 5/2004 | Cummings |
| 6,755,855 B2 | 6/2004 | Yurek et al. |
| 6,773,446 B1 | 8/2004 | Dwyer et al. |
| 6,776,791 B1 | 8/2004 | Stallings et al. |
| 6,802,849 B2 | 10/2004 | Blaeser et al. |
| 6,860,898 B2 | 3/2005 | Stack et al. |
| 6,939,352 B2 | 9/2005 | Buzzard et al. |
| 6,942,682 B2 | 9/2005 | Vrba et al. |
| 6,951,675 B2 | 10/2005 | Chin et al. |
| 7,001,423 B2 | 2/2006 | Euteneuer et al. |
| 7,387,640 B2 | 6/2008 | Cummings |
| 7,632,296 B2 | 12/2009 | Malewicz |
| 7,740,652 B2 | 6/2010 | Gerdts et al. |
| 8,075,607 B2 * | 12/2011 | Melsheimer | A61F 2/95 623/2.11 |
| 8,128,676 B2 | 3/2012 | Cummings |
| 8,152,818 B2 | 4/2012 | Gunderson |
| 8,403,982 B2 | 3/2013 | Giannetti et al. |
| 8,784,468 B2 | 7/2014 | Gerdts et al. |
| 9,084,692 B2 | 7/2015 | Hacker |
| 9,220,619 B2 | 12/2015 | Ramos et al. |
| 10,449,073 B1 | 10/2019 | Longo et al. |
| 2001/0034548 A1 | 10/2001 | Vrba et al. |
| 2001/0034549 A1 | 10/2001 | Bartholf et al. |
| 2001/0037141 A1 | 11/2001 | Yee et al. |
| 2002/0052641 A1 | 5/2002 | Monroe et al. |
| 2002/0058951 A1 | 5/2002 | Fiedler |
| 2002/0082550 A1 | 6/2002 | Hamilton et al. |
| 2002/0095203 A1 | 7/2002 | Thompson et al. |
| 2002/0103525 A1 | 8/2002 | Cummings |
| 2002/0165523 A1 | 11/2002 | Chin et al. |
| 2003/0163156 A1 | 8/2003 | Hebert et al. |
| 2004/0098083 A1 | 5/2004 | Tran et al. |
| 2004/0148009 A1 | 7/2004 | Buzzard et al. |
| 2004/0215317 A1 | 10/2004 | Cummings |
| 2004/0267348 A1 | 12/2004 | Gunderson et al. |
| 2005/0027345 A1 | 2/2005 | Horan et al. |
| 2005/0080476 A1 | 4/2005 | Gunderson et al. |
| 2005/0149159 A1 | 7/2005 | Andreas et al. |
| 2005/0154439 A1 | 7/2005 | Gunderson |
| 2005/0182475 A1 | 8/2005 | Jen et al. |
| 2005/0192657 A1 | 9/2005 | Colen et al. |
| 2005/0240254 A1 | 10/2005 | Austin |
| 2005/0256562 A1 | 11/2005 | Clerc et al. |
| 2005/0273151 A1 | 12/2005 | Fulkerson et al. |
| 2006/0009833 A1 | 1/2006 | Chobotov et al. |
| 2006/0030923 A1 | 2/2006 | Gunderson |
| 2006/0041302 A1 | 2/2006 | Malewicz |
| 2006/0074477 A1 | 4/2006 | Berthiaume et al. |

(56) References Cited

U.S. PATENT DOCUMENTS

| | | |
|---|---|---|
| 2006/0190069 A1 | 8/2006 | Baker-Janis et al. |
| 2006/0229697 A1 | 10/2006 | Gerdts et al. |
| 2006/0292300 A1 | 12/2006 | Tan |
| 2007/0060999 A1 | 3/2007 | Randall et al. |
| 2007/0142894 A1 | 6/2007 | Moore et al. |
| 2007/0208350 A1 | 9/2007 | Gunderson |
| 2007/0282420 A1 | 12/2007 | Gunderson |
| 2008/0188920 A1 | 8/2008 | Moberg et al. |
| 2008/0294267 A1 | 11/2008 | Chanduszko |
| 2009/0036967 A1 | 2/2009 | Cummings |
| 2009/0192584 A1 | 7/2009 | Gerdts et al. |
| 2010/0256727 A1 | 10/2010 | Gerdts et al. |
| 2017/0065415 A1 | 3/2017 | Rupp et al. |
| 2018/0193605 A1 | 7/2018 | Shumer et al. |

FOREIGN PATENT DOCUMENTS

| | | |
|---|---|---|
| EP | 0775470 A1 | 5/1997 |
| EP | 0633756 B1 | 12/1998 |
| EP | 0820259 B1 | 2/2003 |
| EP | 1385450 B1 | 3/2007 |
| EP | 1844739 A1 | 10/2007 |
| JP | H1189942 A | 4/1999 |
| JP | 2017064520 A | 4/2017 |
| WO | 9717899 A1 | 5/1997 |
| WO | 9949808 A1 | 10/1999 |
| WO | 0018330 A1 | 4/2000 |
| WO | 0023139 A1 | 4/2000 |
| WO | 0027309 A1 | 5/2000 |
| WO | 0067828 A1 | 11/2000 |
| WO | 0071059 A1 | 11/2000 |
| WO | 0176676 A2 | 10/2001 |
| WO | 02056953 A2 | 7/2002 |
| WO | 2004098692 A1 | 11/2004 |
| WO | 2005020856 A2 | 3/2005 |
| WO | 2005107644 A1 | 11/2005 |
| WO | 2005112824 A1 | 12/2005 |
| WO | 2006036472 A1 | 4/2006 |
| WO | 2007005799 A1 | 1/2007 |
| WO | 2007084370 A1 | 7/2007 |

OTHER PUBLICATIONS

International Search Report and Written Opinion dated May 26, 2020 for International Application No. PCT/US2020/018171, 16 pages.

\* cited by examiner

STENT DELIVERY SYSTEMS

CROSS-REFERENCE TO RELATED APPLICATIONS

This application is a continuation of U.S. patent application Ser. No. 16/790,560, filed Feb. 13, 2020, which claims the benefit of priority under 35 U.S.C. § 119 to U.S. Provisional Application Ser. No. 62/805,133, filed Feb. 13, 2019, the entirety of which is incorporated herein by reference.

TECHNICAL FIELD

The present disclosure pertains to medical devices, and methods for manufacturing medical devices. More particularly, the present disclosure pertains to elongated intracorporeal medical devices including a tubular member connected with other structures, and methods for manufacturing and using such devices.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. A stent delivery system is disclosed. The stent delivery system comprises: an inner member having a stent receiving region; a stent disposed along the stent receiving region; a deployment sheath axially slidable relative to the inner member, the deployment sheath having a proximal end region; a rack coupled to the proximal end region of the deployment sheath; an outer shaft disposed along at least a portion of the deployment sheath; and wherein the deployment sheath is rotatable relative to the inner member, the outer shaft or both.

Alternatively or additionally to any of the embodiments above, the rack includes a coupling member designed to couple the deployment sheath to the rack.

Alternatively or additionally to any of the embodiments above, the coupling member includes an annular opening.

Alternatively or additionally to any of the embodiments above, the coupling member includes an interrupted annular opening.

Alternatively or additionally to any of the embodiments above, further comprising a sleeve disposed along the proximal end region of the deployment sheath, the sleeve being designed to limit distal translation of the deployment sheath relative to the rack.

Alternatively or additionally to any of the embodiments above, the rack includes a first coupling member and a second coupling member, wherein the first coupling member and the second coupling member are designed for coupling the deployment sheath to the rack, and wherein the proximal end region of the deployment sheath thereto is disposed adjacent to the first coupling member and the second coupling member.

Alternatively or additionally to any of the embodiments above, further comprising a sleeve disposed along the proximal end region of the deployment sheath, the sleeve being designed to limit distal translation of the deployment sheath relative to the rack.

Alternatively or additionally to any of the embodiments above, the sleeve is disposed between the first coupling member and the second coupling member.

Alternatively or additionally to any of the embodiments above, at least a portion of the rack is disposed within a handle coupled to the deployment sheath.

Alternatively or additionally to any of the embodiments above, the rack includes a toothed section having plurality of teeth and wherein the toothed section is designed to engage a gear disposed within the handle.

Alternatively or additionally to any of the embodiments above, the rack is designed to shift between a first configuration and a second configuration, and wherein the toothed section engages an upper region of the gear when the rack in in the first configuration.

Alternatively or additionally to any of the embodiments above, the toothed section engages a lower region of the gear when the rack in in the second configuration.

Alternatively or additionally to any of the embodiments above, the handle includes a rack track with a curved region and wherein at least a section of the rack extends along the curved region when the rack is in the second configuration.

A stent delivery system is disclosed. The stent delivery system comprises: an inner member having a stent receiving region; a stent disposed along the stent receiving region; a deployment sheath axially slidable relative to the inner member; a flexible rack coupled to a proximal end region of the deployment sheath with a rotatable linkage; and an outer shaft disposed along at least a portion of the deployment sheath.

Alternatively or additionally to any of the embodiments above, the rotatable linkage includes an annular opening.

Alternatively or additionally to any of the embodiments above, the rotatable linkage includes an interrupted annular opening.

Alternatively or additionally to any of the embodiments above, the rotatable linkage includes a sleeve disposed along the proximal end region of the deployment sheath, the sleeve being designed to limit distal translation of the deployment sheath relative to the flexible rack.

A stent delivery system is disclosed. The stent delivery system comprises: an inner member having a stent receiving region; a stent disposed along the stent receiving region; a deployment sheath axially slidable relative to the inner member; a flexible rack coupled to a proximal end region of the deployment sheath; wherein the flexible rack includes a first coupling member and a second coupling member; a sleeve disposed along the deployment sheath and positioned between the first coupling member and the second coupling member; and an outer shaft disposed along at least a portion of the deployment sheath.

Alternatively or additionally to any of the embodiments above, the first coupling member, the second coupling member, or both include an annular opening.

Alternatively or additionally to any of the embodiments above, the first coupling member, the second coupling member, or both include an interrupted annular opening.

A stent delivery system is disclosed. The stent delivery system comprises: an inner member having a stent receiving region; a stent disposed along the stent receiving region; a deployment sheath axially slidable relative to the inner member, the deployment sheath having a proximal end region; a handle coupled to the deployment sheath; a rack coupled to the proximal end region of the deployment sheath; wherein the rack is designed to shift between a first configuration and a second configuration; wherein the deployment sheath covers the stent when the rack is in the first configuration; wherein the deployment sheath is proximally retracted to deploy the stent when the rack is in the second configuration; wherein the proximal end region of the rack is disposed within the handle when the rack is in either the first configuration or the second configuration; and an outer shaft disposed along at least a portion of the deployment sheath.

Alternatively or additionally to any of the embodiments above, the rack includes a coupling member designed to couple the deployment sheath to the rack.

Alternatively or additionally to any of the embodiments above, the coupling member includes an annular opening.

Alternatively or additionally to any of the embodiments above, the coupling member includes an interrupted annular opening.

Alternatively or additionally to any of the embodiments above, further comprising a sleeve disposed along the proximal end region of the deployment sheath, the sleeve being designed to limit distal translation of the deployment sheath relative to the rack.

Alternatively or additionally to any of the embodiments above, the rack includes a first coupling member and a second coupling member, wherein the first coupling member and the second coupling member are designed for coupling the deployment sheath to the rack, and wherein the proximal end region of the deployment sheath thereto is disposed adjacent to the first coupling member and the second coupling member.

Alternatively or additionally to any of the embodiments above, further comprising a sleeve disposed along the proximal end region of the deployment sheath, the sleeve being designed to limit distal translation of the deployment sheath relative to the rack.

Alternatively or additionally to any of the embodiments above, the sleeve is disposed between the first coupling member and the second coupling member.

Alternatively or additionally to any of the embodiments above, the rack includes a toothed section having plurality of teeth and wherein the toothed section is designed to engage a gear disposed within the handle.

Alternatively or additionally to any of the embodiments above, the toothed section engages an upper region of the gear when the rack in in the first configuration.

Alternatively or additionally to any of the embodiments above, the toothed section engages a lower region of the gear when the rack in in the second configuration.

Alternatively or additionally to any of the embodiments above, the handle includes a rack track with a curved region and wherein at least a section of the rack extends along the curved region when the rack is in the second configuration.

Alternatively or additionally to any of the embodiments above, the deployment sheath is rotatable relative to the inner member, the outer shaft or both.

A stent delivery system is disclosed. The stent delivery system comprises: an inner member having a stent receiving region; a stent disposed along the stent receiving region; a deployment sheath axially slidable relative to the inner member, the deployment sheath having a proximal end region; a handle coupled to the deployment sheath, the handle having a rack track with a curved region; a flexible rack coupled to the proximal end region of the deployment sheath, the flexible rack being designed to move along the rack track; and an outer shaft disposed along at least a portion of the deployment sheath.

Alternatively or additionally to any of the embodiments above, the deployment sheath is rotatable relative to the inner member, the outer shaft or both.

Alternatively or additionally to any of the embodiments above, the flexible rack includes a toothed section having plurality of teeth and wherein the toothed section is designed to engage a gear disposed within the handle.

Alternatively or additionally to any of the embodiments above, the flexible rack is designed to shift between a first configuration and a second configuration, and wherein the toothed section engages an upper region of the gear when the flexible rack in in the first configuration.

Alternatively or additionally to any of the embodiments above, the toothed section engages a lower region of the gear when the flexible rack in in the second configuration.

Alternatively or additionally to any of the embodiments above, at least a section of the flexible rack extends along the curved region when the flexible rack is in the second configuration.

A method for deploying a stent is disclosed. The method comprises: disposing a stent delivery system along a body lumen, the stent delivery system comprising: an inner member having a stent receiving region, a stent disposed along the stent receiving region, a deployment sheath axially slidable relative to the inner member, the deployment sheath having a proximal end region, a handle coupled to the deployment sheath, the handle having a rack track with a curved region, a flexible rack coupled to the proximal end region of the deployment sheath, the flexible rack being designed to move along the rack track, wherein the flexible rack includes a toothed section having plurality of teeth and wherein the toothed section is designed to engage a gear disposed within the handle, and an outer shaft disposed along at least a portion of the deployment sheath; proximally retracting the deployment sheath, wherein proximally retracting the deployment sheath includes shifting the flexible rack from a first configuration where the toothed section engages an upper portion of the gear to a second configuration where the toothed section engages a lower portion of the gear.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
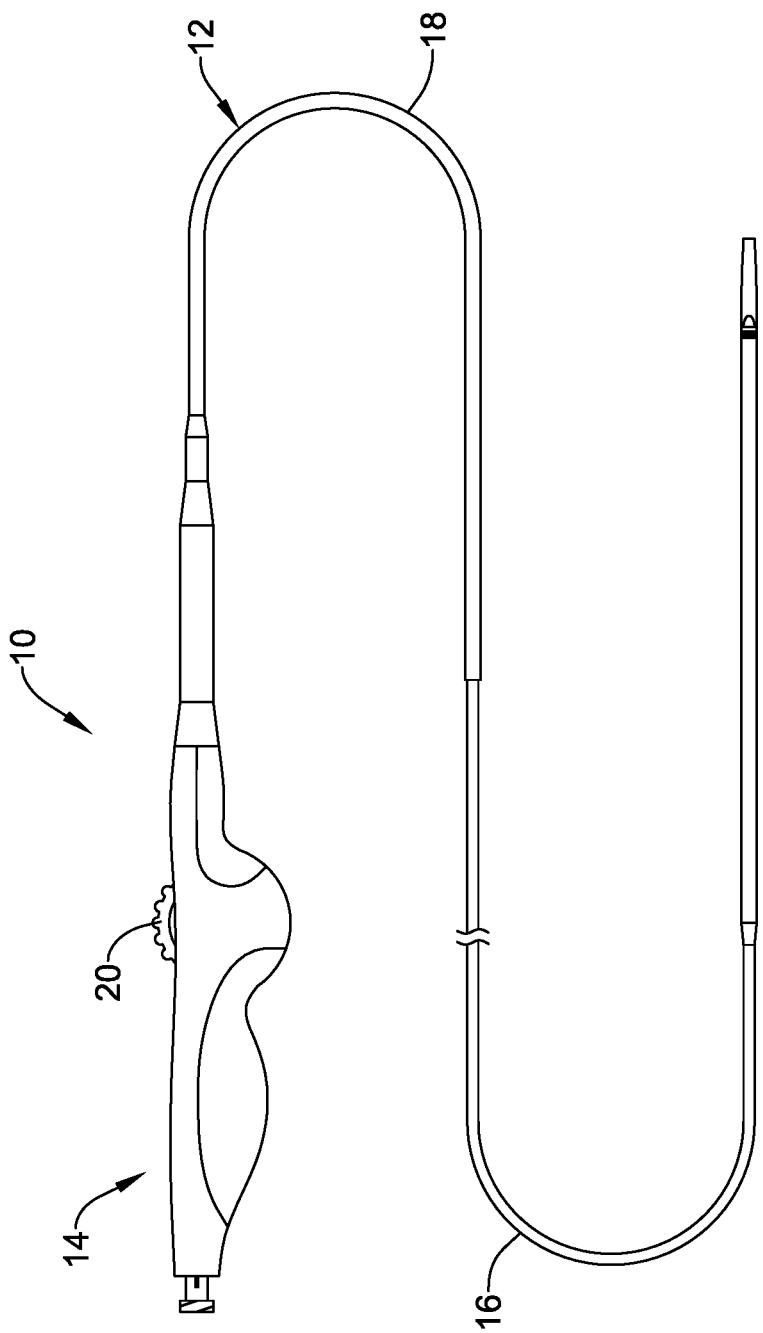
FIG. 1 is a side view of an example stent delivery system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 illustrates an example stent delivery system 10. The system 10 may include an elongate shaft 12 and a handle 14 coupled to the shaft 12. The shaft 12 may include an inner shaft or liner (not shown in FIG. 1, can be seen in FIG. 2), a deployment sheath 16, and an outer shaft 18. In general, the system 10 may be used to deliver a stent, graft, endoprosthesis or the like to an area of interest within a body lumen of a patient. The body lumen may be a blood vessel located near the heart (e.g., within or near a cardiac vessel), within a peripheral vessel, within a neurological vessel, or at any other suitable location. Deployment of the stent may include proximal retraction of a deployment sheath 16, which overlies or otherwise is designed to cover the stent during delivery of the stent. Retraction of the deployment sheath 16 may include the actuation of an actuation member 20 generally disposed at the handle 14. In the example illustrated in FIG. 1, the actuation member 20 is a thumb wheel that can be rotated by a clinician in order to accomplish proximal retraction of the deployment sheath 16. Numerous other actuation members are contemplated.

Figure 2:
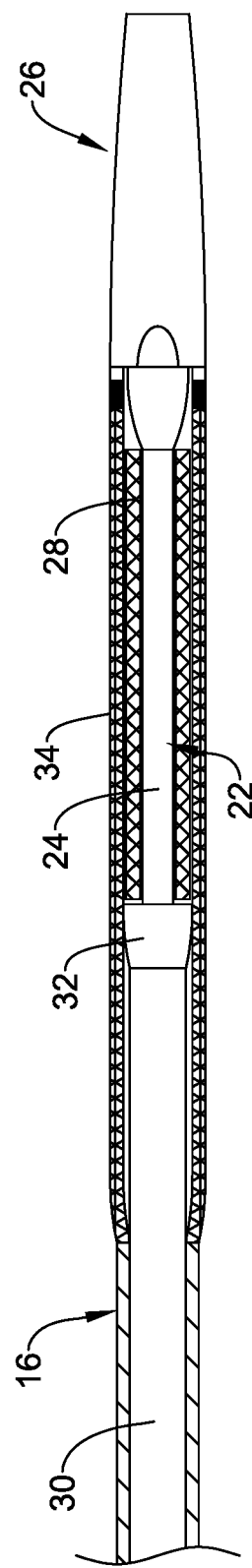
FIG. 2 is a partial cross-section view of a portion of an example stent delivery system.

Some of the other features of the system 10 are shown in FIG. 2. For example, the system 10 may include an inner liner or member 22. The inner member 22 may define a guidewire lumen and may include a stent receiving region 24 about which a stent 28 may be disposed. In at least some instances, the stent 28 is a self-expanding stent and may be made from a suitable material such as a nickel-titanium alloy. A distal tip 26 may be attached to or otherwise disposed at the distal end of the inner member 22. The distal tip 26 may generally have a rounded or smooth shape that provides a generally atraumatic distal end to system 10. A bumper shaft or member 30 may be disposed about the inner member 22. The bumper shaft 30 may include a bumper region 32. In general, the bumper region 32 may function as a proximal bumper during deployment of the stent 28. Also depicted in FIG. 2 is that the deployment sheath 16 may include an enlarged distal section 34. In some instances, the system 10 may include features of the systems disclosed in U.S. Pat. Nos. 8,784,468, 9,084,692, and 9,220,619, the entire discloses of which are herein incorporated by reference.

Stent delivery systems are typically used along with a guidewire (e.g., the systems typically threaded over a guidewire). It may be desirable for a clinician to maintain the position of the guidewire relative to the system (e.g., relative to the handle). It may also be desirable to reduce the likelihood that the guidewire may become kinked, for example at locations adjacent to the handle. The systems disclosed herein are designed to allow a clinician to maintain the position of the guidewire relative to the handle, reduce the likelihood of kinking the guidewire adjacent to the handle, and the like. Other features are also contemplated.

The deployment sheath 16 may be coupled to a flexible rack 36 as depicted in FIGS. FIGS. 3A-3D. The flexible rack 36 may include a toothed section 38 including a plurality of teeth. As the name suggests, the flexible rack 36 may be formed from a flexible/bendable material and, in general, the flexible rack 36 may be designed to travel within a rack guide 40 having a rack track or groove 42 formed therein. In general, the rack guide and/or rack track 42 allows for the flexible rack 36 to be moved/translated relatively great distances while being contained within the handle 14 (e.g., in a manner such that the flexible rack 36 does not exit the proximal end of the handle 14 when in either an initial or first configuration or when in other configurations including those where the deployment sheath 16 is retracted in order to deploy the stent 28). This may provide greater access to a guidewire extending through the system 10 (e.g., and out from a proximal end of the handle 14) and allow a clinician to maintain the position of the guidewire relative to the system 10 and to reduce/avoid kinking the guidewire.

Movement of the flexible rack 36 may result in movement of the deployment sheath 16 (e.g., which may include proximal retraction of the deployment sheath 16 and/or deployment of the stent 28). In order to shift the position of the flexible rack 36 (and the deployment sheath 16), the toothed section 38 of the flexible rack 36 may engage a gear 44 coupled to the actuation member 20. Accordingly, rotation of the actuation member 20 may result in proximal retraction of the flexible rack 36 and proximal retraction of the deployment sheath 16.

Figure 3A:
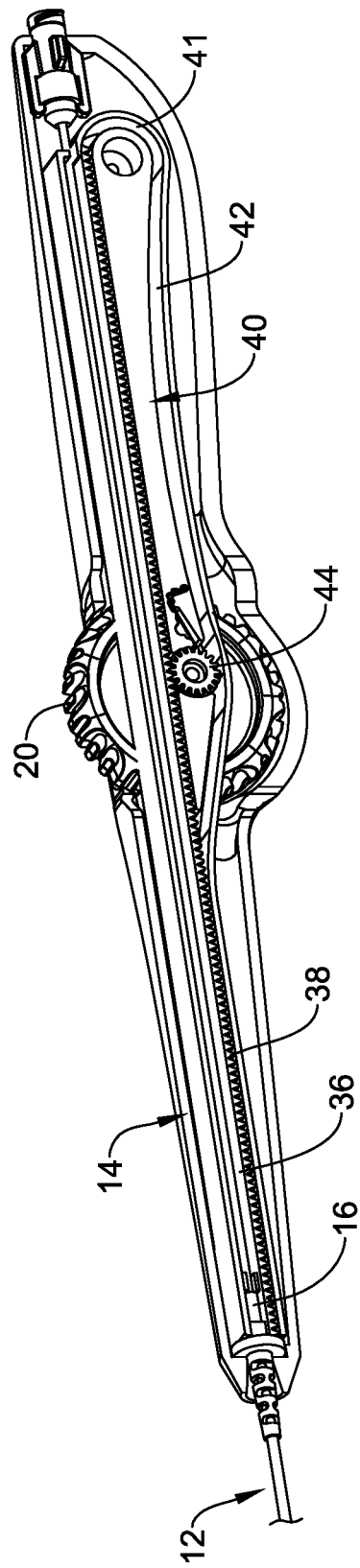
FIGS. 3A-3D illustrate a portion of an example stent delivery system.
Figure 3B:
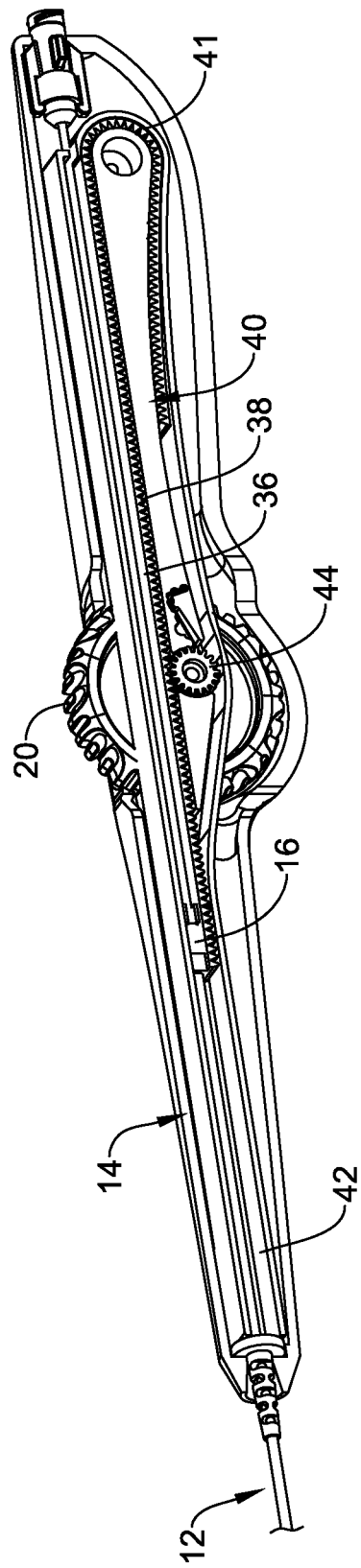

The flexible rack 36 may be designed to shift between a plurality of positions/configurations. When the flexible rack 36 is in a first or initial configuration as shown in FIG. 3A, the toothed section 38 may be engaged with an upper or top portion of the gear 44. Rotation of the actuation member 20 may cause the flexible rack 36 to be proximally retracted or "pulled" as shown in FIG. 3B, resulting in proximal retraction of the deployment sheath 16. This may result in the flexible rack 36 extending through a curved region 41 of the rack track 42 (and/or the rack guide 40). In some instances, such an arrangement may be understood to be an intermediate or second arrangement/configuration.

Figure 3C:
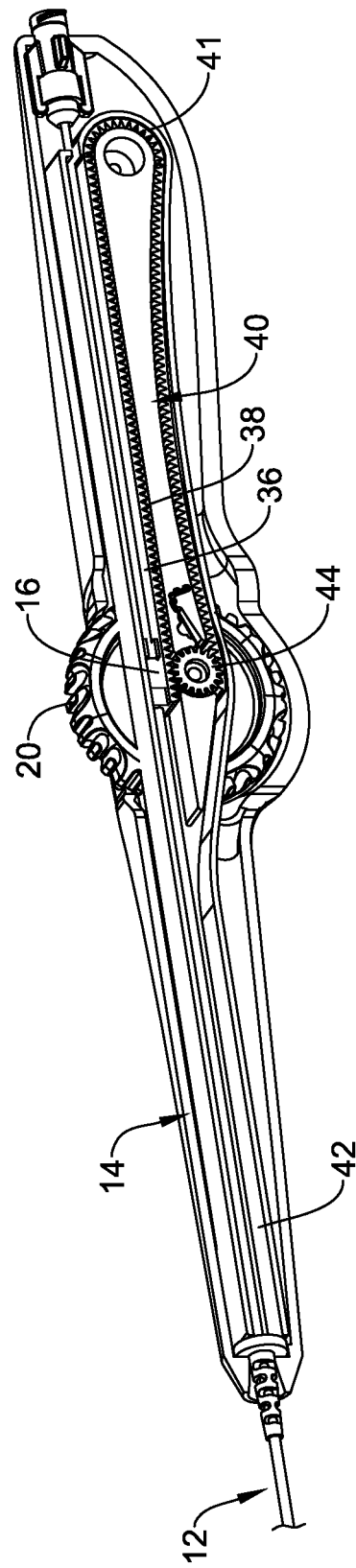
Figure 3D:
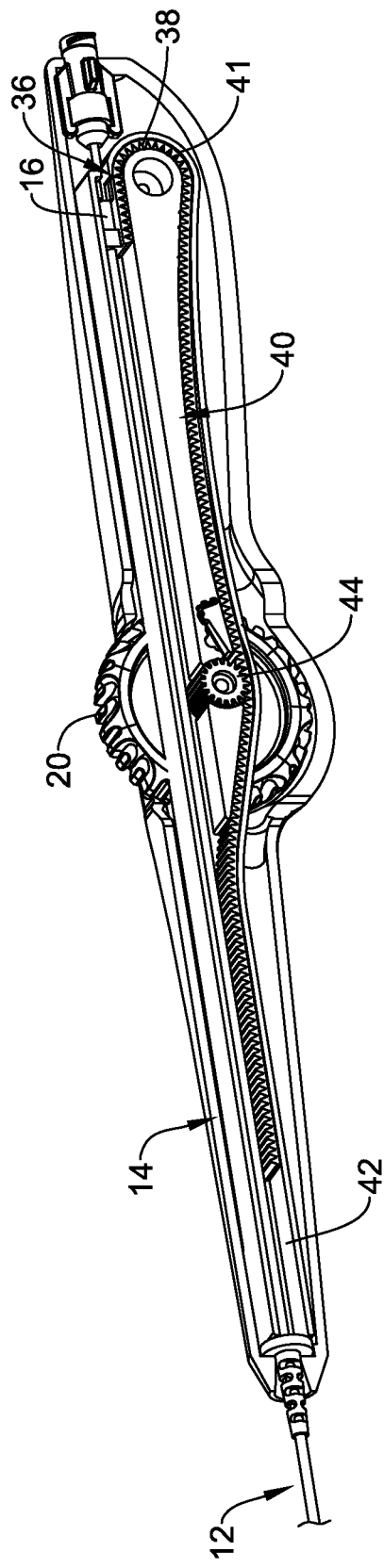

As the flexible rack 36 is further retracted, the toothed section 38 may come into contact with the lower portion of the gear 44 as shown in FIG. 3C. The toothed section 38 of the flexible rack 36 may disengage from the upper portion of the gear 44 may shift to a configuration where the lower portion of the gear 44 continues to retract the deployment sheath 16 while "pushing" the flexible rack 36 as depicted in FIG. 3D. In some instances, such an arrangement may be understood to be a deployed or third arrangement/configuration.

Figure 4:
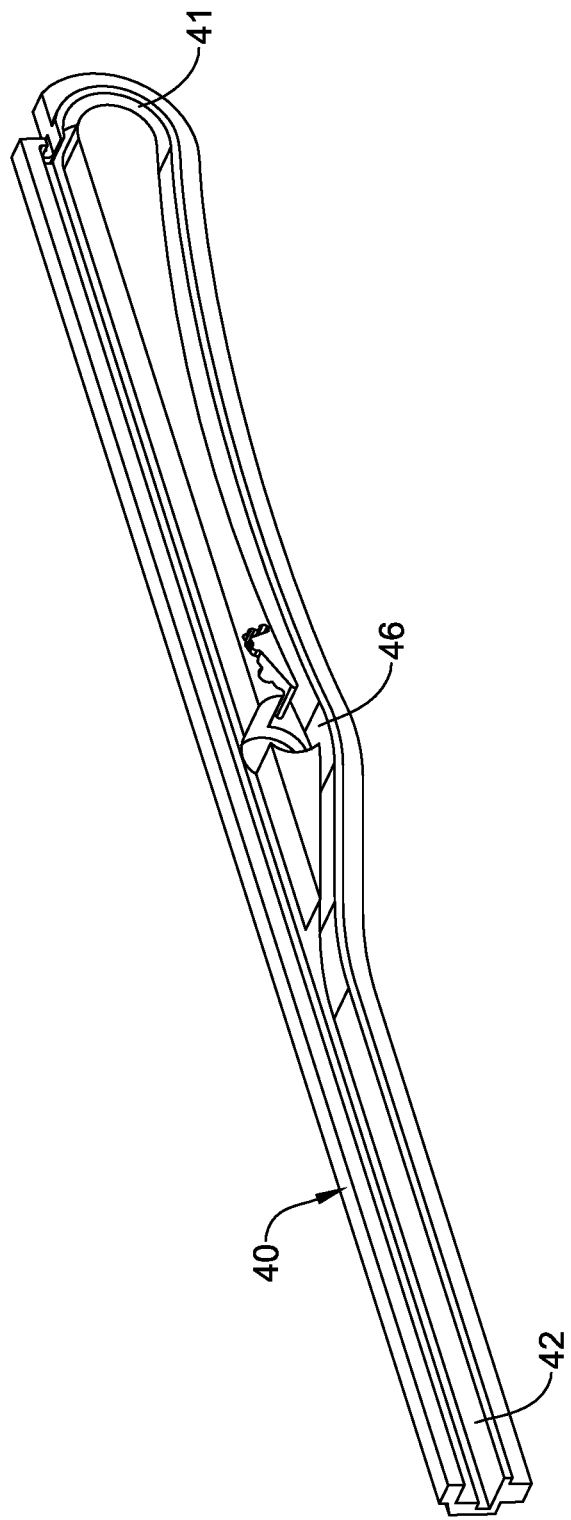
FIG. 4 illustrates a portion of an example stent delivery system.

FIG. 4 is a perspective view of the rack guide 40. Here, the rack track 42 can be seen along with the curved region 41 and a transition region 46. The rack guide 40 may be separate structure that can be inserted into the handle housing so as to provide the rack track 42 within the handle 14. Alternatively, the rack guide 40 and/or rack track 42 may be formed integrally within the handle 14.

In some instances, bending of the system 10 around curves/bends in the anatomy can cause buildup of forces in one or more components of the shaft 12. For example, torsional forces may be exerted on the deployment sheath 16 while the system 10 is bent through the tortuous anatomy. The buildup of forces could increase the amount of force required to retract the deployment sheath 16, decrease the tensile strength of the deployment sheath 16, and/or the like. The system 10 is designed to include a number of additional features that help to reduce the buildup of forces, reduce the amount of force needed to proximally retract the deployment sheath 16, increase the tensile strength of the deployment sheath 16, and the like.

Figure 5:
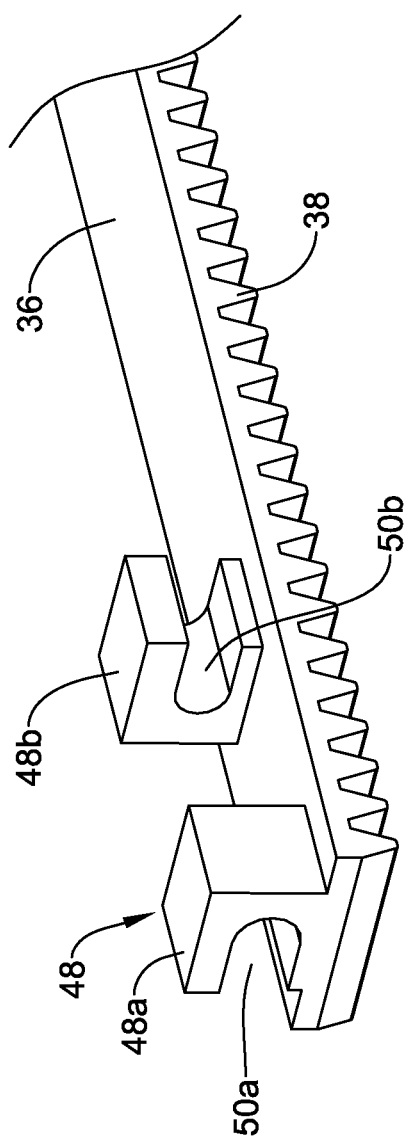
FIG. 5 illustrates a portion of an example stent delivery system.
Figure 6:
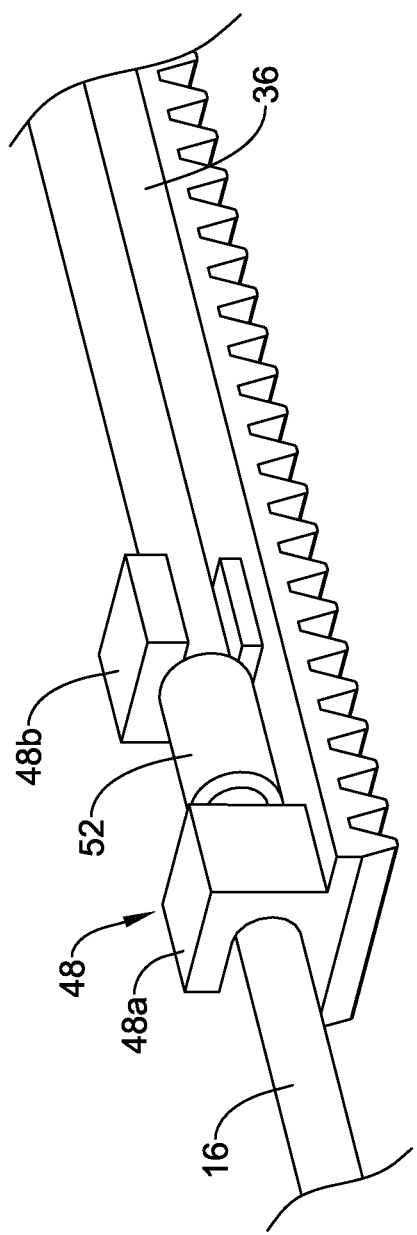
FIG. 6 illustrates a portion of an example stent delivery system.

In at least some instances, the deployment sheath 16 is coupled to the flexible rack 36 by a coupling member 48 as shown in FIGS. 5-6. In general, the coupling member 48 may be described as a rotatable linkage designed so that the deployment sheath 16 is rotatable relative to the inner member 22, the outer shaft 18, or both. As shown in FIG. 5, the coupling member 48 include a first coupling member or portion 48a and a second coupling member or portion 48b. The form of the coupling member 48 (and/or the form of the first portion 48a and the second portion 48b thereof) may vary. In some instances, the first portion 48a may include a first opening or passageway 50a. The second portion 48b may include a second opening or passageway 50b. The openings 50a, 50b may be understood to be annular or ring-like in shape. In some of these and in other instances, the openings 50a, 50b may be understood to be partially annular or as being interrupted. For the purposes of this disclosure, an interrupted annular opening or section may be understood as an opening or portion defined by a surface or structure that forms an incomplete or partially open ring. Some examples of interrupted annular shapes may include "C" shapes, "U" shapes, and the like. Further, while be described as being annular or interrupted annular shapes, such connotations do not necessarily mean that the shapes resemble circles (or interrupted circles) as shapes with curves or bends that are not precisely circular in shape may be understood as having the annular features/shapes disclosed herein. In the example depicted in FIGS. 5-6, the openings 50a, 50b may be described as interrupted annular openings where the interruptions or openings in the wall of the portions 48a, 48b are oriented opposite one another (e.g., the interruptions or openings in the wall of the portions 48a, 48b are oriented on opposing sides).

The deployment sheath 16 may be coupled to the coupling member 48 as shown in FIG. 6. For example, the deployment sheath 16 may extend through the first opening 50a and through the second opening 50b. In some instances, a sleeve 52 may be coupled to the deployment sheath 16 to substantially prevent the deployment sheath from shifting distally (e.g. the sleeve 52 may limit distal translation of the deployment sheath 16) relative to the coupling member 48 while allowing the deployment sheath 16 to rotate relative to the coupling member 48 (and/or the flexible rack 36 and/or other components of the system 10). In this example, the sleeve 52 is disposed between the first portion 48a and the second portion 48b.

Figure 7:
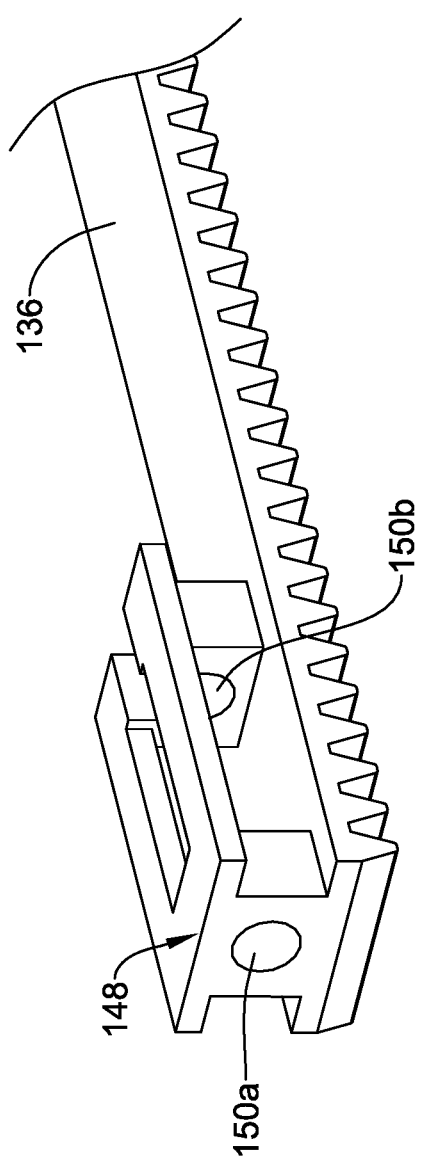
FIG. 7 illustrates a portion of an example stent delivery system.

The form of the coupling member 48 may vary. FIGS. 7-11 illustrate a number of alternative coupling members that may be similar in form and function to the coupling member 48. For example, FIG. 7 illustrates a flexible rack 136 with a coupling member 148. In this example, the coupling member 148 includes a first opening 150a and a second opening 150b. The first opening 150a may be an annular opening (e.g., forming a complete ring) and the second opening 150b may be an interrupted annular opening (e.g., forming an interrupted ring). The deployment sheath 16 may be coupled to the coupling member 148 in a suitable manner such as by extending the deployment sheath 16 through the openings 150a, 150b and by disposing a sleeve (e.g., such as the sleeve 52) onto the deployment sheath 16.

Figure 8:
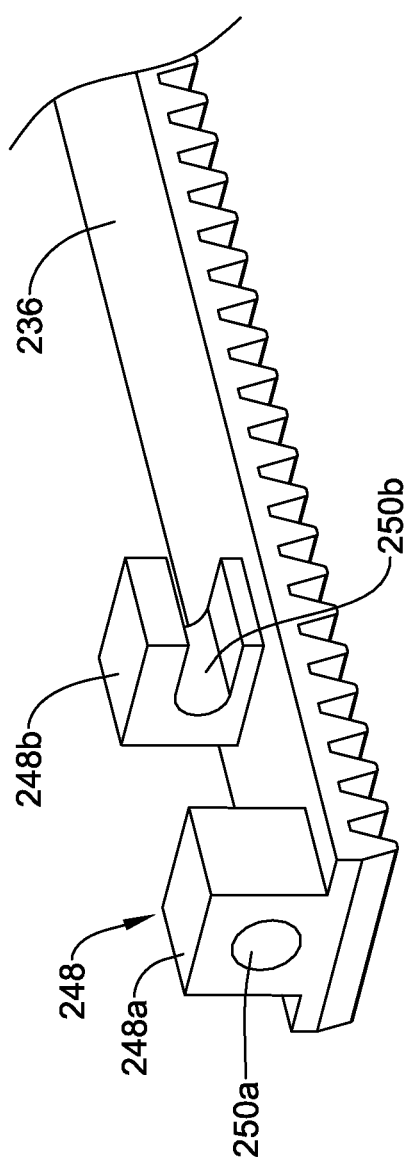
FIG. 8 illustrates a portion of an example stent delivery system.

FIG. 8 illustrates a flexible rack 236 with a coupling member 248. The coupling member 248 includes a first portion 248a and second portion 248b. A first opening 250a may be formed in the first portion 248a. A second opening 250b may be formed in the second portion 248a. In this example, the first opening 250a may be an annular opening (e.g., forming a complete ring) and the second opening 250b may be an interrupted annular opening (e.g., forming an interrupted ring). The deployment sheath 16 may be coupled to the coupling member 248 in a suitable manner such as by extending the deployment sheath 16 through the openings 250a, 250b and by disposing a sleeve (e.g., such as the sleeve 52) onto the deployment sheath 16.

Figure 9:
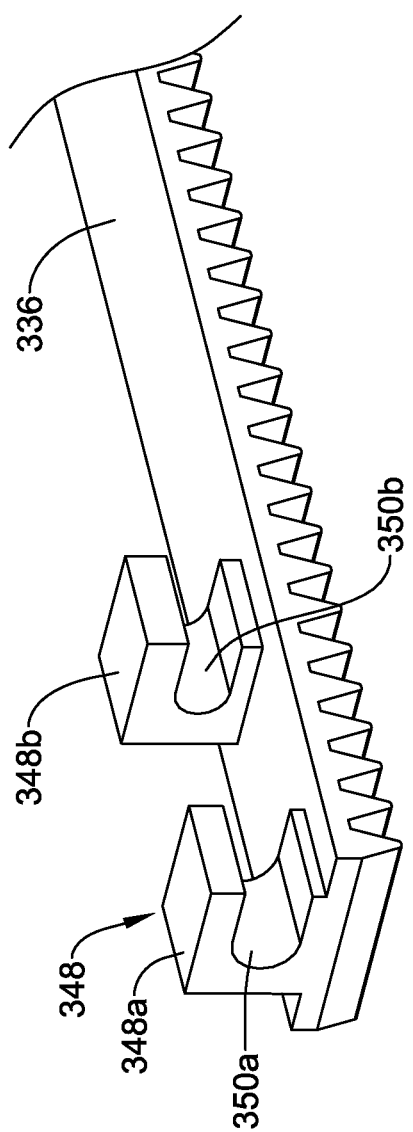
FIG. 9 illustrates a portion of an example stent delivery system.

FIG. 9 illustrates a flexible rack 336 with a coupling member 348. The coupling member 348 includes a first portion 348a and second portion 348b. A first opening 350a may be formed in the first portion 348a. A second opening 350b may be formed in the second portion 348a. In this example, the first opening 350a may be an interrupted annular opening (e.g., forming an interrupted ring) and the second opening 350b may be an interrupted annular opening (e.g., forming an interrupted ring). In this example, the interruptions of the openings 350a, 350b are oriented on the same side. The deployment sheath 16 may be coupled to the coupling member 348 in a suitable manner such as by extending the deployment sheath 16 through the openings 350a, 350b and by disposing a sleeve (e.g., such as the sleeve 52) onto the deployment sheath 16.

Figure 10:
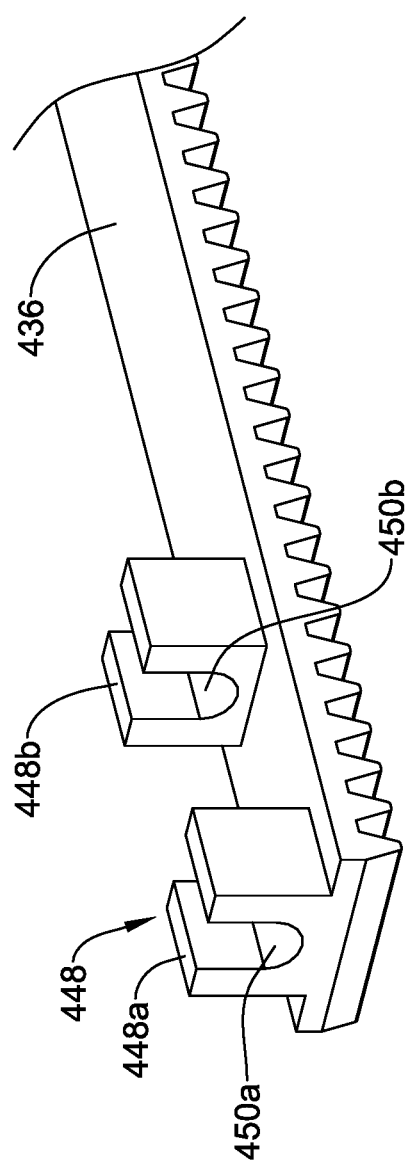
FIG. 10 illustrates a portion of an example stent delivery system.

FIG. 10 illustrates a flexible rack 436 with a coupling member 448. The coupling member 448 includes a first portion 448a and second portion 448b. A first opening 450a may be formed in the first portion 448a. A second opening 450b may be formed in the second portion 448a. In this example, the first opening 450a may be an interrupted annular opening (e.g., forming an interrupted ring) and the second opening 450b may be an interrupted annular opening (e.g., forming an interrupted ring). In this example, the interruptions of the openings 450a, 450b are oriented on the same side (e.g., oriented "upward"). The deployment sheath 16 may be coupled to the coupling member 448 in a suitable manner such as by extending the deployment sheath 16 through the openings 450a, 450b and by disposing a sleeve (e.g., such as the sleeve 52) onto the deployment sheath 16.

Figure 11:
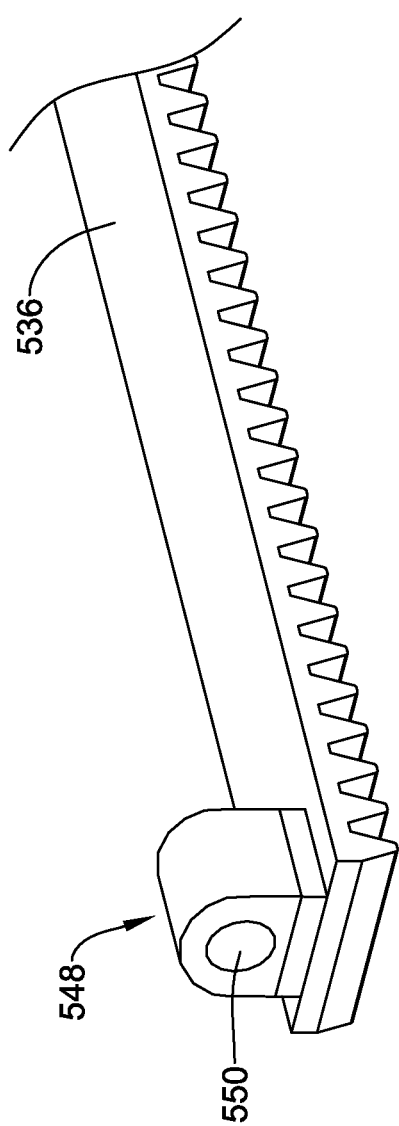
FIG. 11 illustrates a portion of an example stent delivery system.

FIG. 11 illustrates a flexible rack 536 with a coupling member 548. A first opening 550 may be formed in the coupling member 548. In this example, the opening 450a may be an annular opening (e.g., forming a complete ring). The deployment sheath 16 may be coupled to the coupling member 548 in a suitable manner such as by extending the deployment sheath 16 through the opening 550 and by disposing a sleeve (e.g., such as the sleeve 52) onto the deployment sheath 16.

The materials that can be used for the various components of the system 10 (and/or other systems disclosed herein) may include those commonly associated with medical devices. For simplicity purposes, the following discussion makes reference to the shaft 12. However, this is not intended to limit the devices and methods described herein, as the discussion may be applied to other components, devices, or systems disclosed herein.

The shaft 12 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyetherester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the shaft 12 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the shaft 12 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the shaft 12 to achieve the same result.

In some embodiments, a degree of Magnetic Resonance Imaging (MRI) compatibility is imparted into the shaft 12. For example, the shaft 12, or portions thereof, may be made of a material that does not substantially distort the image and create substantial artifacts (e.g., gaps in the image). Certain ferromagnetic materials, for example, may not be suitable because they may create artifacts in an MRI image. The shaft 12, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A stent delivery system, comprising:
    an inner member having a stent receiving region configured to have a stent disposed thereon;
    a deployment sheath axially slidable relative to the inner member, the deployment sheath having a proximal end region;
    a handle coupled to the proximal end region of the deployment sheath;
    a rack guide disposed within the handle;
    a channel formed within the rack guide, the channel extending continuously from a distal end region of the handle and a proximal end region of the handle;
    wherein the channel includes a curved region disposed adjacent to the proximal end region of the handle where the channel curves and extends distally;
    a rack extending along the channel, the rack having a first end coupled to the proximal end region of the deployment sheath and a second end free from attachment with the first end; and
    wherein the deployment sheath is rotatable relative to the inner member.

2. The stent delivery system of claim 1, further comprising an outer shaft disposed along at least a portion of the deployment sheath.

3. The stent delivery system of claim 2, wherein the deployment sheath is rotatable relative to the outer shaft.

4. The stent delivery system of claim 1, wherein the rack includes a coupling member designed to couple the deployment sheath to the rack.

5. The stent delivery system of claim 4, wherein the coupling member includes an annular opening.

6. The stent delivery system of claim 4, wherein the coupling member includes an interrupted annular opening.

7. The stent delivery system of claim 4, further comprising a sleeve disposed along the proximal end region of the deployment sheath, the sleeve being designed to limit distal translation of the deployment sheath relative to the rack.

8. The stent delivery system of claim 1, wherein the rack includes a first coupling member and a second coupling member, wherein the first coupling member and the second coupling member are designed for coupling the deployment sheath to the rack, and wherein the proximal end region of the deployment sheath thereto is disposed adjacent to the first coupling member and the second coupling member.

9. The stent delivery system of claim 8, further comprising a sleeve disposed along the proximal end region of the deployment sheath, the sleeve being designed to limit distal translation of the deployment sheath relative to the rack.

10. The stent delivery system of claim 9, wherein the sleeve is disposed between the first coupling member and the second coupling member.

11. The stent delivery system of claim 1, wherein the rack includes a toothed section having plurality of teeth and wherein the toothed section is designed to engage a gear disposed within the handle.

12. The stent delivery system of claim 11, wherein the rack is designed to shift between a first configuration and a second configuration, and wherein the toothed section engages an upper region of the gear when the rack is in the first configuration.

13. The stent delivery system of claim 12, wherein the toothed section engages a lower region of the gear when the rack is in the second configuration.

14. The stent delivery system of claim 12, wherein at least a section of the rack extends along the curved region when the rack is in the second configuration.

15. A stent delivery system, comprising:
    an inner member having a stent receiving region;
    a stent disposed along the stent receiving region;
    a deployment sheath axially slidable relative to the inner member;
    a handle coupled to the deployment sheath, the handle having a rack guide extending continuously between a proximal end region of the handle and a distal end region of the handle;
    a flexible rack coupled to a proximal end region of the deployment sheath;
    wherein the flexible rack extends along a channel formed by the rack guide;
    wherein the rack guide includes a curved region disposed adjacent to the proximal end region of the handle where the channel curves and extends distally; and
    an outer shaft disposed along at least a portion of the deployment sheath.

16. The stent delivery system of claim 15, wherein the flexible rack is coupled to the proximal end region of the deployment sheath with a rotatable linkage.

17. A stent delivery system, comprising:
    a handle;
    an inner member having a stent receiving region, the inner member being coupled to the handle;
    a deployment sheath axially slidable relative to the inner member;
    a flexible rack coupled to a proximal end region of the deployment sheath, the flexible rack having a first surface with a plurality of teeth formed therein and a second generally planar surface opposite the first surface;
    wherein the flexible rack is configured to extend along a channel formed by a rack guide disposed within the handle;
    wherein the channel includes a first end disposed adjacent to a distal end region of the handle and a curved region disposed adjacent to a proximal end region of the handle; and
    wherein the channel is continuous between the first end and the curved region.

18. The stent delivery system of claim 17, further comprising an outer shaft disposed along at least a portion of the deployment sheath.

19. The stent delivery system of claim 17, wherein the flexible rack is coupled to the proximal end region of the deployment sheath with a rotatable linkage.

* * * * *